United States Patent
Kuramoto

(10) Patent No.: US 10,441,150 B2
(45) Date of Patent: Oct. 15, 2019

(54) ENDOSCOPE SYSTEM AND OPERATING METHOD THEREOF

(71) Applicant: FUJIFILM Corporation, Tokyo (JP)

(72) Inventor: Masayuki Kuramoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1299 days.

(21) Appl. No.: 14/475,901

(22) Filed: Sep. 3, 2014

(65) Prior Publication Data

US 2015/0087903 A1    Mar. 26, 2015

(30) Foreign Application Priority Data

Sep. 23, 2013    (JP) .................................. 2013-196305

(51) Int. Cl.
*A61B 1/06* (2006.01)
*A61B 1/00* (2006.01)
*A61B 1/045* (2006.01)

(52) U.S. Cl.
CPC .......... *A61B 1/0684* (2013.01); *A61B 1/0002* (2013.01); *A61B 1/00006* (2013.01);
(Continued)

(58) Field of Classification Search
CPC ............ A61B 1/00006; A61B 1/00009; A61B 1/0002; A61B 1/045; A61B 1/0638;
(Continued)

(56) References Cited

U.S. PATENT DOCUMENTS

| 5,864,361 A | 1/1999 | Sekiya et al. |
| 2003/0001952 A1 | 1/2003 | Iida et al. |

(Continued)

FOREIGN PATENT DOCUMENTS

| DE | 10226582 A1 | 12/2002 |
| JP | 8-126607 A | 5/1996 |

(Continued)

OTHER PUBLICATIONS

Japanese Notice of Reasons for Refusal dated Sep. 2, 2015, for Japanese Application No. 2013-196305 with the English translation.
(Continued)

*Primary Examiner* — Timothy J Neal
*Assistant Examiner* — William B Chou
(74) *Attorney, Agent, or Firm* — Birch, Stewart, Kolasch & Birch, LLP

(57) ABSTRACT

A V-LED, B-LED, G-LED and R-LED for an endoscope are all driven to apply normal light to an object of interest in a body. An image sensor images the illuminated object and outputs an RGB image signal. A measurement sensor measures a light amount of red light from the R-LED. A light source controller acquires a current value for the R-LED according to a light amount signal from the measurement sensor and a target light amount signal for the R-LED. A normal color converter and the R-LED receive a current of the current value. Each LUT_Mij in the normal color converter is referred to for outputting a matrix coefficient according to the current value of the R-LED. The RGB image signal is converted into a processed image signal by matrix operation according to the matrix coefficient.

14 Claims, 13 Drawing Sheets

(52) U.S. Cl.
CPC ...... *A61B 1/00009* (2013.01); *A61B 1/00059* (2013.01); *A61B 1/045* (2013.01); *A61B 1/0638* (2013.01)

(58) Field of Classification Search
CPC ................ A61B 1/0669; A61B 1/0684; G02B 19/0061; G02B 23/2461
USPC ....... 600/109, 110, 153, 160, 176, 177, 178, 600/179, 180, 181, 182
See application file for complete search history.

(56) References Cited

U.S. PATENT DOCUMENTS

| | | | |
|---|---|---|---|
| 2004/0125203 A1 | 7/2004 | Kobayashi | |
| 2004/0257438 A1* | 12/2004 | Doguchi et al. | H04N 7/18 348/65 |
| 2005/0068427 A1 | 3/2005 | Sudo et al. | |
| 2007/0123751 A1 | 5/2007 | Takahashi | |
| 2008/0232131 A1* | 9/2008 | Suda | A61B 1/0669 362/574 |
| 2009/0023991 A1* | 1/2009 | Gono et al. | A61B 1/04 600/109 |
| 2010/0274082 A1* | 10/2010 | Iguchi et al. | A61B 1/04 600/109 |
| 2010/0277087 A1* | 11/2010 | Ikeda | A61B 1/0669 315/250 |
| 2011/0187842 A1* | 8/2011 | Yamazaki | A61B 1/00057 348/68 |
| 2011/0237885 A1 | 9/2011 | Matsubara | |
| 2011/0273549 A1* | 11/2011 | Kase | A61B 1/00147 348/68 |
| 2012/0130175 A1* | 5/2012 | Koshikawa | A61B 1/0638 600/178 |
| 2013/0150713 A1* | 6/2013 | Takei | A61B 1/00009 600/431 |
| 2013/0150728 A1* | 6/2013 | Takei | A61B 6/52 600/476 |
| 2014/0054450 A1* | 2/2014 | Shirota | G02B 23/26 250/226 |

FOREIGN PATENT DOCUMENTS

| | | |
|---|---|---|
| JP | 2006-341078 A | 12/2006 |
| JP | 2010-158413 A | 7/2010 |
| JP | 2011-200410 A | 10/2011 |
| JP | 4787032 B2 | 10/2011 |
| JP | 2012-223376 A | 11/2012 |

OTHER PUBLICATIONS

Chinese Office Action and Search Report, dated Nov. 14, 2016, for counterpart Chinese Application No. 201410479619.5, along with an English translation.
Chinese Office Action dated Jun. 16, 2017, for Chinese Application No. 201410479619.5, together with an English translation.
Extended European Search Report, dated Jan. 30, 2015, for European Application No. 14183405.1.

* cited by examiner

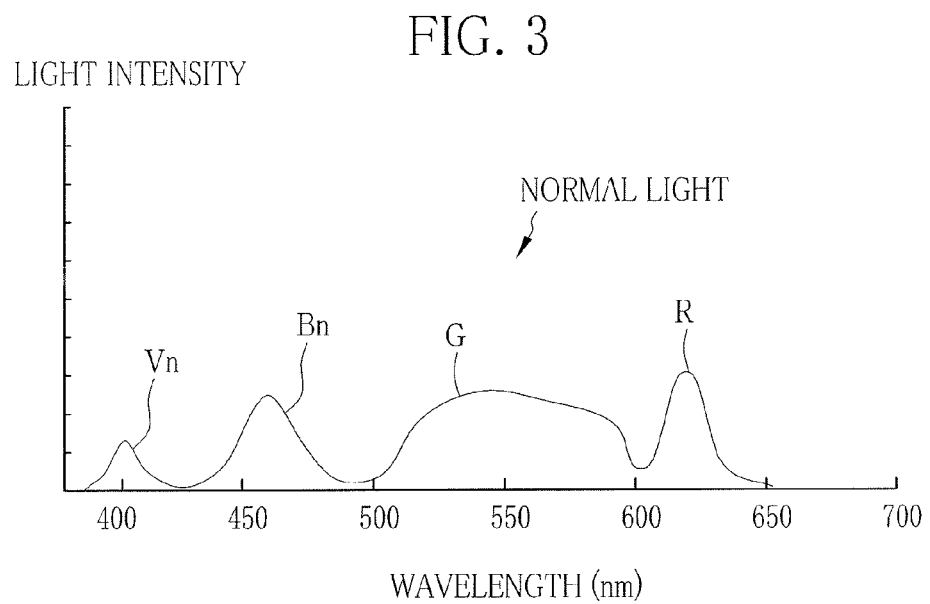
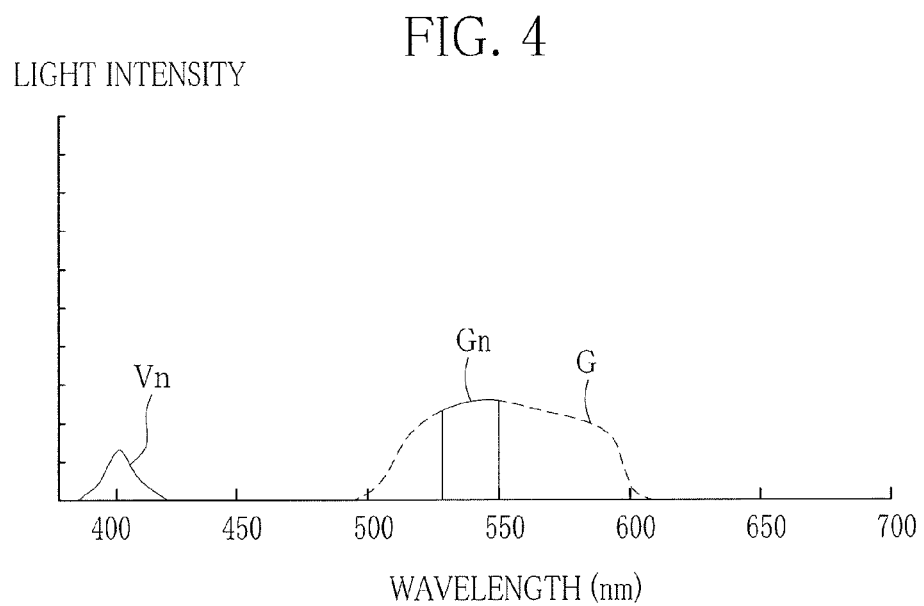

| RGB IMAGE SIGNAL | | | COLOR-CONVERTED RGB IMAGE SIGNAL | | |
|---|---|---|---|---|---|
| R0 | G0 | B0 | R0 | G0 | B0 |
| ⋮ | ⋮ | ⋮ | ⋮ | ⋮ | ⋮ |
| R255 | G255 | B255 | R240 | G255 | B255 |

ENDOSCOPE SYSTEM AND OPERATING METHOD THEREOF

CROSS-REFERENCE TO RELATED APPLICATION

The present application claims priority under 35 U.S.C. § 119 to Japanese Patent Application No. 2013-196305 filed 23 Sep. 2013. The above application is hereby expressly incorporated by reference, in its entirety, into the present application.

BACKGROUND OF THE INVENTION

1. Field of the Invention

The present invention relates to an endoscope system that irradiates the inside of a body cavity with light from a plurality of semiconductor light sources such as LEDs, and an operating method of the endoscope system.

2. Description Related to the Prior Art

In medical service, diagnosis and treatment using an endoscope system, having a light source apparatus, an endoscope, and a processing apparatus, have become widespread. As the light source apparatus of the endoscope system, a broadband light source such as a xenon lamp has been widely used, and furthermore, a semiconductor light source including an LED (light emitting diode), an LD (laser diode), and the like are becoming available.

It is known that a light amount of the semiconductor light source varies with temperature variation, aging degradation, and the like. In the case of using a combination of a plurality of color semiconductor light sources, the ratio in the emitted light amount between the plural color semiconductor light sources is necessarily set at a predetermined value even at any brightness. However, variation in the emitted light amount of any color of the semiconductor light sources due to the temperature variation or the like makes the ratio go out of the set value to create a change in a color tone.

For this reason, according to Japanese Patent Laid-Open Publication No. 2010-158413, in order to prevent variation in the light amount, a light receiver such as a sensor detects the light amount, and the operation of the semiconductor light sources is controlled based on the detection result, such that color temperature of emission light is made constant. According to Japanese Patent No. 4787032, in order to prevent variation in the light amount, a temperature sensor detects the temperature of the semiconductor light source, and a processing apparatus changes a gain by which an image signal is multiplied in accordance with the detection result of the temperature sensor. Changing the gain prevents variation in the image signal caused by variation in the light amount. However, Japanese Patent No. 4787032 cannot detect the aging degradation.

It is known that a temperature drift (wavelength shift) occurs in the semiconductor light source in accordance with a current value applied to the semiconductor light source, in other words, light intensity, in addition to the variation in the emitted light amount as described above. In the case of the R-LED, as illustrated in FIG. 18, a peak wavelength shifts to a long wavelength side with an increase in the light intensity ("low", "medium" and "high" represent the magnitude of the light intensity in FIG. 18 and also FIG. 20). The wavelength shift changes a color tone of an endoscopic image, and hence variously affects imaging quality.

For example, in imaging using a dye e.g. crystal violet, as illustrated in FIG. 19, an output value (reflected light amount) of the crystal violet goes out of linear proportion at a high level of the light intensity of the R-LED. Especially, redness becomes strong as the emitted light amount of the R-LED increases, just as in the case of telephoto imaging. This is because, as illustrated in FIG. 20, in addition to that the peak wavelength of the R-LED shifts to the long wavelength side with an increase in the light intensity, the reflectivity of the crystal violet gradually increases on the longer wavelength side than 600 nm, and therefore, the reflected light amount of the R-LED becomes too large. The strong redness at a portion having the crystal violet due to the wavelength shift may cause a doctor to confuse the crystal violet with bleeding tissue.

The change in the color tone e.g. a change of color of the crystal violet associated with the wavelength shift, as described above, needs correcting in accordance with the wavelength shift. Neither the light source correction as described in Japanese Patent Laid-Open Publication No. 2010-158413 nor the gain modification as described in Japanese Patent No. 4787032 is adequate for such a correction.

SUMMARY OF THE INVENTION

In view of the foregoing problems, an object of the present invention is to provide an endoscope system that can correct a change in a color tone associated with a wavelength shift of a semiconductor light source and the like, and a method for operating the endoscope system.

In order to achieve the above and other objects and advantages of this invention, an endoscope system includes a semiconductor light source apparatus for emitting light to illuminate an object in a body cavity. A measurement sensor measures a light amount of the light. A light source controller sets a drive value of the light source apparatus according to the light amount of the light from the measurement sensor. An image sensor images the object illuminated with the light to obtain a first color image signal of a color image. A color converter performs color conversion of the first color image signal into a second color image signal, and adjusts a setting of the color conversion according to the set drive value of the light source apparatus.

Preferably, the color conversion includes a matrix operation of converting the first color image signal into the second color image signal according to a first matrix coefficient, and the first matrix coefficient is changeable according to the set drive value.

Preferably, furthermore, a table memory stores a drive value of the light source apparatus and the first matrix coefficient associated with the drive value, the table memory being accessed for the matrix operation by the color converter.

Preferably, furthermore, a table memory stores a particular drive value usable in the light source apparatus and predetermined with discreteness, and the first matrix coefficient associated with the particular drive value. A storage medium stores an actual drive value for the light source apparatus in smaller steps than the particular drive value, and the first matrix coefficient associated with the actual drive value. In case a moving image mode is set, the color converter refers to the particular drive value in the table memory according to the set drive value to read out the first matrix coefficient, and in case a still image mode is set, the color converter refers to the set drive value in the storage memory to read out the first matrix coefficient.

In another preferred embodiment, furthermore, a table memory stores a particular drive value usable in the light source apparatus and predetermined with discreteness, and the first matrix coefficient associated with the particular drive value. In case a moving image mode is set, the color converter refers to the particular drive value in the table memory according to the set drive value to read out the first matrix coefficient. In case a still image mode is set, the color converter interpolates the first matrix coefficient from the table memory by use of the set drive value, to acquire an interpolated value of the first matrix coefficient.

In still another preferred embodiment, in the matrix operation, the first color image signal is further processed in a matrix control according to a second matrix coefficient different from the first matrix coefficient, and the second matrix coefficient is variable according to spectral sensitivity of the image sensor.

Preferably, the light source apparatus includes a plurality of semiconductor light sources of colors for applying the light to the object one after another in relation to the colors. The color converter obtains the second matrix coefficient according to the first color image signal generated upon imaging of the image sensor with the light of the colors.

Preferably, furthermore, a memory stores product ID data of the endoscope having the image sensor and the second matrix coefficient associated with the product ID data, the memory being accessed for the matrix operation by the color converter.

Preferably, furthermore, a table memory stores the first color image signal and the second color image signal associated with the first color image signal, the table memory being accessed for the color conversion by the color converter. The table memory is associated with each one of levels of a drive value of the light source apparatus.

Preferably, the light source apparatus includes an LED.

Preferably, the light source apparatus includes at least blue, green and red light sources, the measurement sensor measures the light amount of the red light source, and the light source controller sets the set drive value of the red light source.

In another preferred embodiment, the light source apparatus includes light sources of first to Nth colors where N is an integer, and the measurement sensor is constituted by first to Nth measurement sensors for respectively measuring the light amount of the light sources of the first to Nth colors.

Also, an operating method of operating an endoscope system is provided, and includes a step of emitting light from a semiconductor light source apparatus to illuminate an object in a body cavity. A light amount of the light is measured. A drive value of the light source apparatus is set according to the light amount of the light. The object illuminated with the light is imaged to obtain a first color image signal of a color image. Color conversion of the first color image signal into a second color image signal is performed. A setting of the color conversion is adjusted according to the set drive value of the light source apparatus.

Consequently, it is possible to correct a change in a color tone due to a wavelength shift of the semiconductor light source apparatus, because the setting of the color conversion is adjusted according to a drive value of the light source apparatus.

BRIEF DESCRIPTION OF THE DRAWINGS

The above objects and advantages of the present invention will become more apparent from the following detailed description when read in connection with the accompanying drawings, in which:

FIG. 3 is a graph illustrating an emission spectrum of normal light;

FIG. 4 is a graph illustrating emission spectra of narrow band violet light Vn and narrow band green light Gn;

DETAILED DESCRIPTION OF THE
PREFERRED EMBODIMENT(S) OF THE
PRESENT INVENTION

First Embodiment

Figure 1:
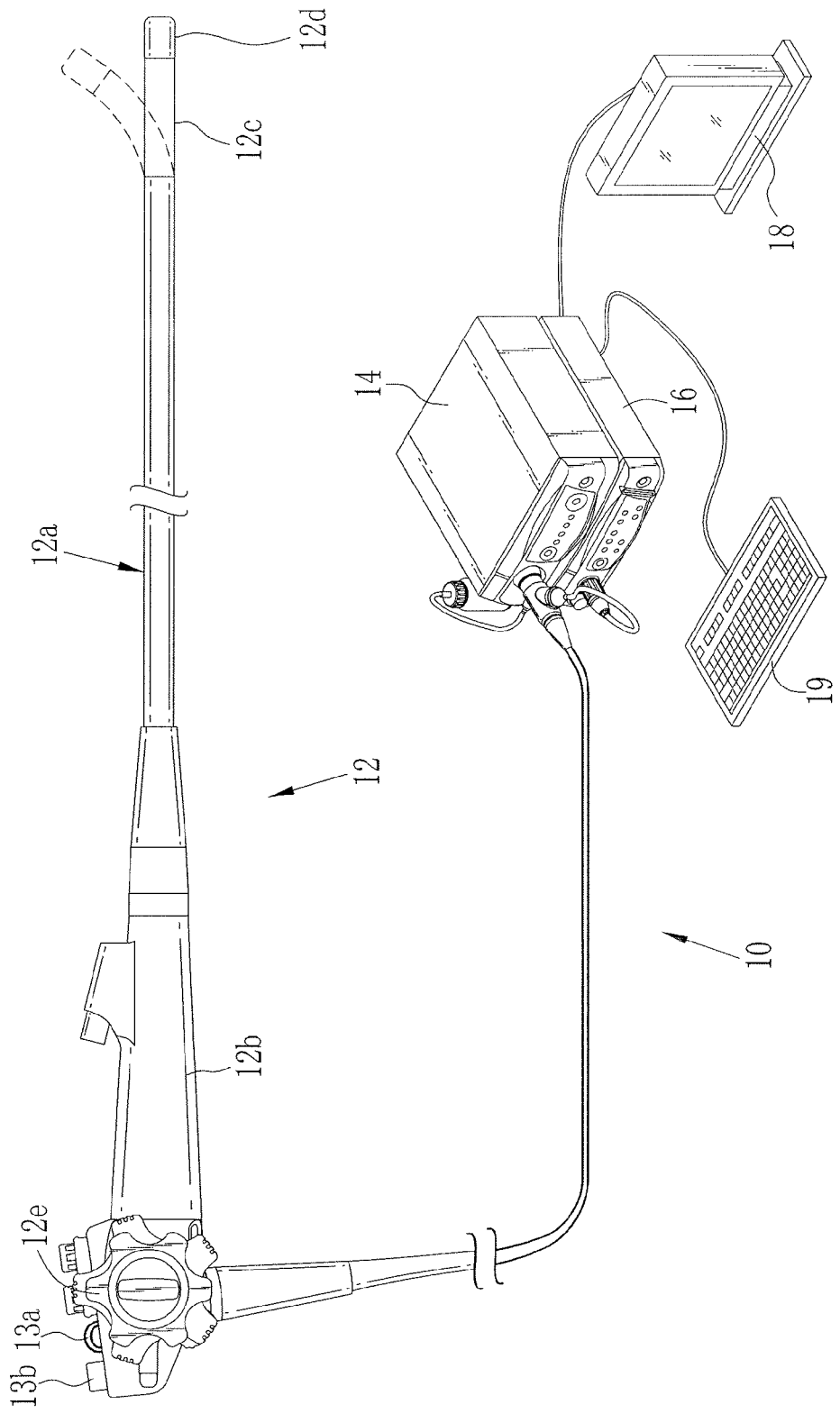
FIG. 1 is a schematic view of an endoscope system.

As illustrated in FIG. 1, an endoscope system 10 according to a first embodiment has an endoscope 12, a light source apparatus 14, a processing apparatus 16, a monitor display panel 18 and a console unit 19. The endoscope 12 is connected optically to the light source apparatus 14, and electrically to the processing apparatus 16. The endoscope 12 has an elongated tube 12a or insertion tube to be introduced into a body cavity, a grip handle 12b provided at a proximal end of the elongated tube 12a, a steering device 12c provided at a distal end of the elongated tube 12a, and a tip device 12d. Operating steering wheels 12e provided on the grip handle 12b flexibly bends the steering device 12c. The bending operation aims the tip device 12d in a desired direction.

The grip handle 12b has a mode selection button 13a and a freeze button 13b, in addition to the steering wheels 12e. The mode selection button 13a is used for switching between two modes, that is, a normal imaging mode and a special imaging mode. In the normal imaging mode, a normal light image produced using white light is displayed on the monitor display panel 18. In the special imaging mode, a special light image produced with light that enhances a particular structure such as a superficial blood vessel by bringing contrast difference from mucous membrane is displayed on the monitor display panel 18.

Pressing the freeze button 13b issues a freeze signal to the processing apparatus 16. The processing apparatus 16 is placed in a moving image mode during waiting for receiving the freeze signal, and displays a moving image of the normal light image, the special light image or the like on the monitor display panel 18. Upon receiving the freeze signal, the processing apparatus 16 is placed from the moving image mode to a still image mode for a predetermined time. During the still image mode, one or more high-quality still images without a blur or the like are chosen from currently captured images, and the chosen still images are stored to a still image memory (not shown).

The processing apparatus 16 is electrically connected to the monitor display panel 18 and the console unit 19. The monitor display panel 18 outputs and displays image information and the like. The console unit 19 functions as a user interface (UI) for receiving input of functional settings and the like. Note that an external storage (not shown) may be connected to the processing apparatus 16 to store the image information and the like.

Figure 2:
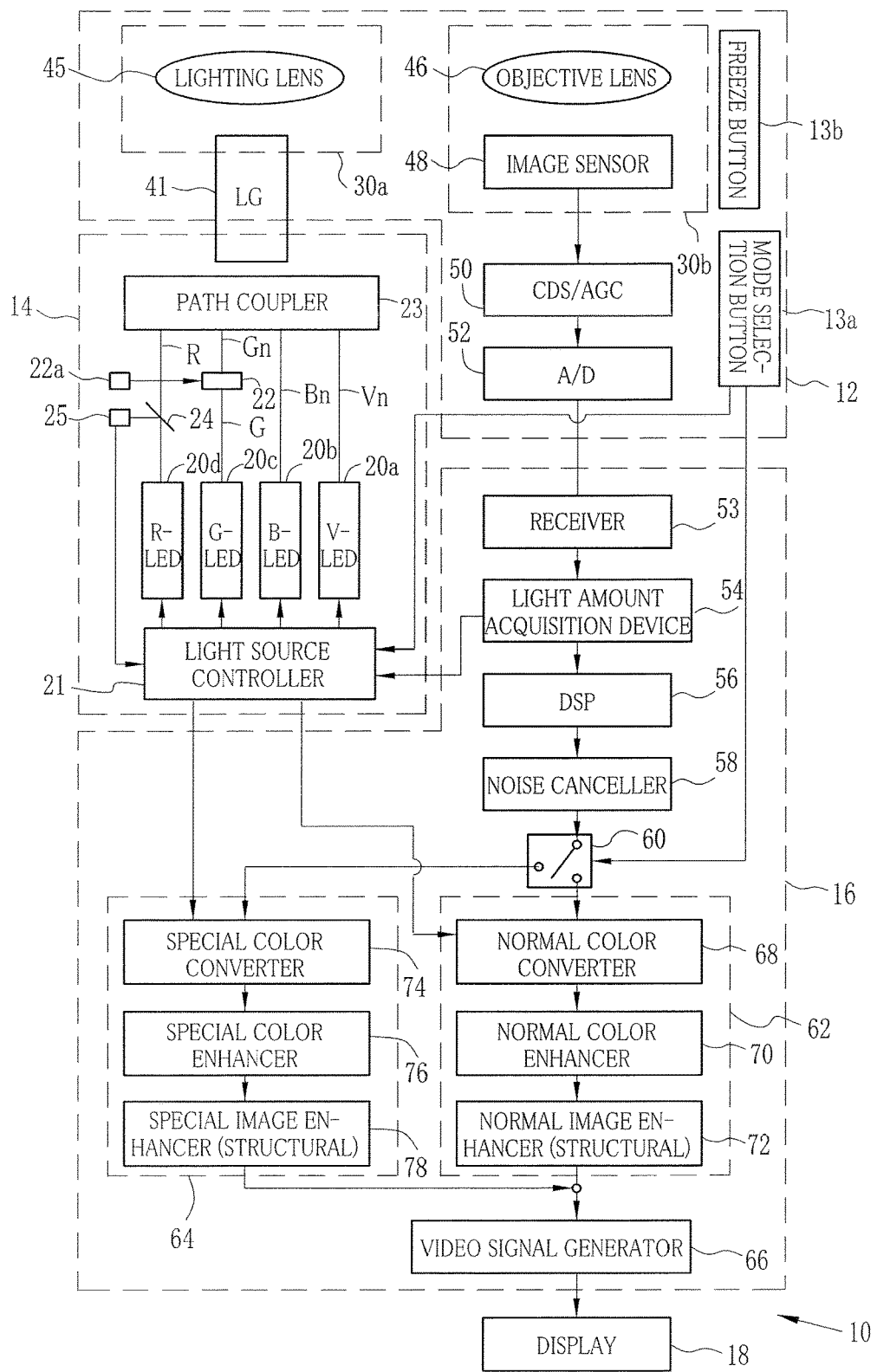
FIG. 2 is a block diagram schematically illustrating the functions of an endoscope system according to a first embodiment.

As illustrated in FIG. 2, the light source apparatus 14 is provided with a violet light emitting diode (V-LED) 20a, a blue light emitting diode (B-LED) 20b, a green light emitting diode (G-LED) 20c and a red light emitting diode (R-LED) 20d (corresponding to semiconductor light sources of the invention), and a light source controller 21 for controlling the operation of the four color LEDs, a narrow band green filter 22 that is inserted into and retracted from an optical path of the G-LED 20c, a path coupler 23 for coupling optical paths of light of four colors emitted from the LEDs 20a-20d, a glass plate 24 or half mirror, and a light amount measurement sensor 25 for a light amount.

The light coupled by the path coupler 23 is applied to an object of interest in a body cavity through a light guide device (LG) 41, which extends through the elongated tube 12a, and a lighting lens 45. The glass plate 24 passes most of red light R emitted from the R-LED 20d to the path coupler 23, and reflects part of the red light R to the measurement sensor 25 by Fresnel reflection. The narrow band green filter 22 is inserted and retracted by a filter driver 22a. Note that laser diodes (LD) may be used instead of the LEDs.

The V-LED 20a emits narrow band violet light Vn having a center wavelength of 405 nm and a wavelength range of 380-440 nm. The B-LED 20b emits narrow band blue-green light Bn having a center wavelength of 460 nm and a wavelength range of 420-500 nm. The G-LED 20c emits green light G having normal distribution of 480-600 nm. The R-LED 20d emits red light R having a center wavelength of 620-630 nm and a wavelength range of 600-650 nm. The narrow band green filter 22 passes narrow band green light Gn of 530-550 nm upon receiving the green light G emitted from the G-LED 20c.

In the normal imaging mode, the light source controller 21 turns on all of the V-LED 20a, the B-LED 20b, the G-LED 20c and the R-LED 20d in a state of retracting the narrow band green filter 22 from the optical path of the G-LED 20c. Thus, as illustrated in FIG. 3, mixture of light of the four colors, that is, the narrow band violet light Vn, the narrow band blue-green light Bn, the green light G and the red light R produces normal light. In the special imaging mode, on the other hand, the V-LED 20a and the G-LED 20c are simultaneously turned on in a state of inserting the narrow band green filter 22 in the optical path of the G-LED 20c. Thus, as illustrated in FIG. 4, the narrow band violet light Vn from the V-LED 20a and the narrow band green light Gn whose wavelength is limited by the narrow band green filter 22 are produced simultaneously.

The light source controller 21 controls an emitted light amount of each of the LEDs 20a-20d by applying predetermined current values (corresponding to a drive value of the LED in the invention) to the V-LED 20a, the B-LED 20b, the G-LED 20c and the R-LED 20d. The current values to be applied to the V-LED 20a, the B-LED 20b and the G-LED 20c are determined in accordance with a target light amount signal outputted from a light amount acquisition device 54 of the processing apparatus 16. The current value to be applied to the R-LED 20d is determined based on the light amount of the red light R measured by the measurement sensor 25, in addition to the target light amount signal. Note that, in this embodiment, the current value "c" to be applied to each of the LEDs 20a-20d is represented by 10 bits, that is, a value of 0-1023.

As illustrated in FIG. 2, the measurement sensor 25 receives the red light R reflected from the glass plate 24, and outputs a light amount signal, corresponding to the light amount of the received red light R, to the light source controller 21. The light source controller 21 compares the light amount signal outputted from the measurement sensor 25 with the target light amount signal outputted from the light amount acquisition device 54 of the processing apparatus 16, and determines the current value "c" to be applied to the R-LED 20d such that the emitted light amount of the R-LED 20d coincides with the target light amount. The determined current value "c" is outputted not only to the R-LED 20d, but also to a normal color converter 68 and a special color converter 74 (color correctors) of the processing apparatus 16 in order to perform matrix operation for preventing a change in a color tone caused by a wavelength shift of the R-LED 20d.

According to this embodiment, as described above, the light amount of the red light R is monitored using the measurement sensor 25, and the emitted light amount of the R-LED 20d is feedback controlled based on the result of monitoring. Thus, even assuming that the emitted light amount of the R-LED 20d varies due to a temperature drift (wavelength shift) or aging degradation, adjustment of the current value to be applied to the R-LED 20d corrects the variation, and therefore, the emitted light amount of the R-LED 20d is always maintained at the target value.

The light guide device 41, which extends through a universal cable for connecting the light source apparatus 14 and the endoscope 12, transmits the light coupled by the path coupler 23 to the tip device 12d of the endoscope 12. Note that a multimode fiber is an available example of the light guide device 41. By way of example, a slender fiber cable having a core diameter of 105 μm, a clad diameter of 125 μm, a diameter φ including a protective layer or jacket material of 0.3-0.5 mm is usable.

The tip device 12d of the endoscope 12 contains a lighting lens system 30a and an imaging lens system 30b. The lighting lens system 30a has the lighting lens 45 through which the light transmitted through the light guide device 41 is applied to an object of interest. The imaging lens system 30b has an objective lens 46 and an image sensor 48. The light reflected from the object of interest is incident upon the image sensor 48 through the objective lens 46. The image sensor 48 forms a reflected image of the object of interest.

Figure 5:
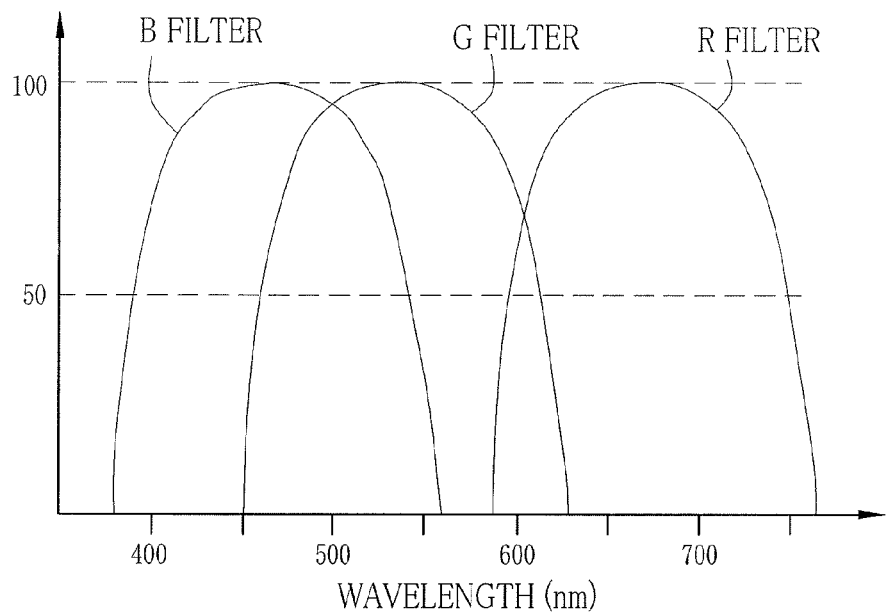
FIG. 5 is a graph illustrating spectral transmittance of a B filter, a G filter and an R filter.

The image sensor 48 is a color imaging device, which captures the reflected image of the object of interest and outputs an image signal. The image sensor 48 is preferably a CCD (charge coupled device) image sensor, a CMOS (complementary metal-oxide semiconductor) image sensor, or the like. The image sensor used in the present invention is a color image sensor for obtaining three-color image signals of R (red), G (green) and B (blue), that is, a so-called RGB image sensor having RGB filters in its imaging surface. As illustrated in FIG. 5, the B filter transmits light with a wavelength of 380-570 nm. The G filter transmits light of 450-630 nm. The R filter transmits light of 580-770 nm.

Figure 6:
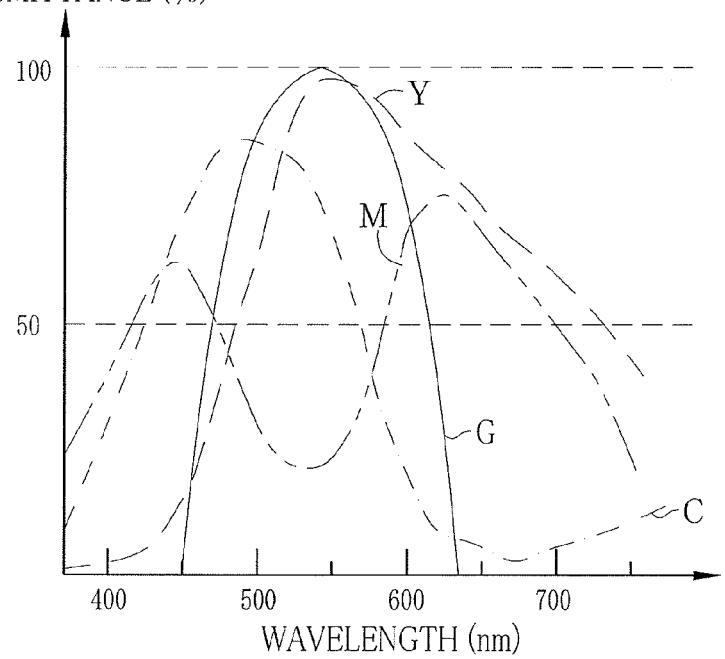
FIG. 6 is a graph illustrating spectral transmittance of complementary color filters of C (cyan), M (magenta), Y (yellow) and G (green)

Note that the image sensor 48 may be a so-called complementary color image sensor having complementary color filters of C (cyan), M (magenta), Y (yellow) and G (green) having spectral transmittance of FIG. 6. In the case of using the complementary color image sensor, the RGB three-color image signals are obtained by color conversion of CMYG four-color image signals. In this case, a color conversion means for making the color conversion from the CMYG four-color image signals into the RGB three-color image signals has to be provided in any of the endoscope 12 and the processing apparatus 16.

As illustrated in FIG. 2, the image signals outputted from the image sensor 48 are sent to a CDS/AGC circuit 50. The CDS/AGC circuit 50 applies correlated double sampling (CDS) and automatic gain control (AGC) to the image signals as analog signals. The image signals subjected to the CDS and the AGC by the CDS/AGC circuit 50 are converted into digital image signals by an A/D converter 52. The converted digital image signals are inputted to the processing apparatus 16.

The processing apparatus 16 includes a receiver 53, the light amount acquisition device 54, a digital signal processor (DSP) 56, a noise canceller 58, a two-way switching device 60, a first image processing device 62 for normal light, a second image processing device 64 for special light, and a video signal generator 66. The receiver 53 receives the digital RGB image signals from the endoscope 12. The R image signal corresponds to a signal outputted from R pixels (pixels having the R filters) of the image sensor 48. The G image signal corresponds to a signal outputted from G pixels (pixels having the G filters) of the image sensor 48. The B image signal corresponds to a signal outputted from B pixels (pixels having the B filters) of the image sensor 48.

The light amount acquisition device 54 calculates an exposure amount based on the digital RGB image signals received by the receiver 53, and calculates a target light amount based on the calculated exposure amount. The light amount acquisition device 54 produces the target light amount signal, which is data of the target light amount of each LED 20a-20d, based on the calculated target light amount and a set light amount ratio between the V-LED 20a, the B-LED 20b, the G-LED 20c and the R-LED 20d.

For example, provided that "P" represents the light amount calculated by the light amount acquisition device 54 and the set light amount ratio is "V-LED:B-LED:G-LED:R-LED=a:b:c:d", then the target light amount of the V-LED 20a is "P×(a/(a+b+c+d))". The target light amount of the B-LED 20b is "P×(b/(a+b+c+d))". The target light amount of the G-LED 20c is "P×(c/(a+b+c+d))", and the target light amount of the R-LED 20d is "P×(d/(a+b+c+d))". Note that the light amount ratio is set by the console unit 19 at different values between the normal and special imaging modes.

The DSP 56 applies gamma correction processing and color correction processing to the RGB image signals. The noise canceller 58 applies noise cancellation (for example, by a moving average method, a median filter method, or the like) to the RGB image signals, after being subjected to the gamma correction and the like by the DSP 56, in order to cancel noise from the RGB image signals. After the noise reduction, the RGB image signals are sent to the two-way switching device 60.

The two-way switching device 60 sends the RGB image signals to the first image processing device 62 assuming that the endoscope system 10 is set in the normal imaging mode by operation of the mode selection button 13a, and sends the RGB image signals to the second image processing device 64 assuming that the endoscope system 10 is set in the special imaging mode.

The first image processing device 62 has the normal color converter 68, a normal color enhancer 70 and a normal image enhancer 72 (structural enhancer), and produces a normal light image in which an object of interest is expressed in normal color of body tissue in vivo. The normal color converter 68 applies color conversion processing to the RGB three channels of digital image signals, and outputs the color-converted RGB image signals. The normal color converter 68 performs matrix operation for the purpose of preventing a change in a color tone caused by a wavelength shift and aging degradation of the R-LED 20d. Details will be described later.

Furthermore, the normal color converter 68 applies gradation conversion processing to the color-converted RGB image signals, and outputs the gradation-converted RGB image signals. The normal color enhancer 70 applies various types of color enhancement processing to the gradation-converted RGB image signals. The normal image enhancer 72 applies structural enhancement processing (image enhancement) to the color-enhanced RGB image signals, for example, sharpness processing, edge enhancement processing and the like. The RGB image signals, after being subjected to the structural enhancement processing by the normal image enhancer 72, are inputted to the video signal generator 66.

Figure 7:
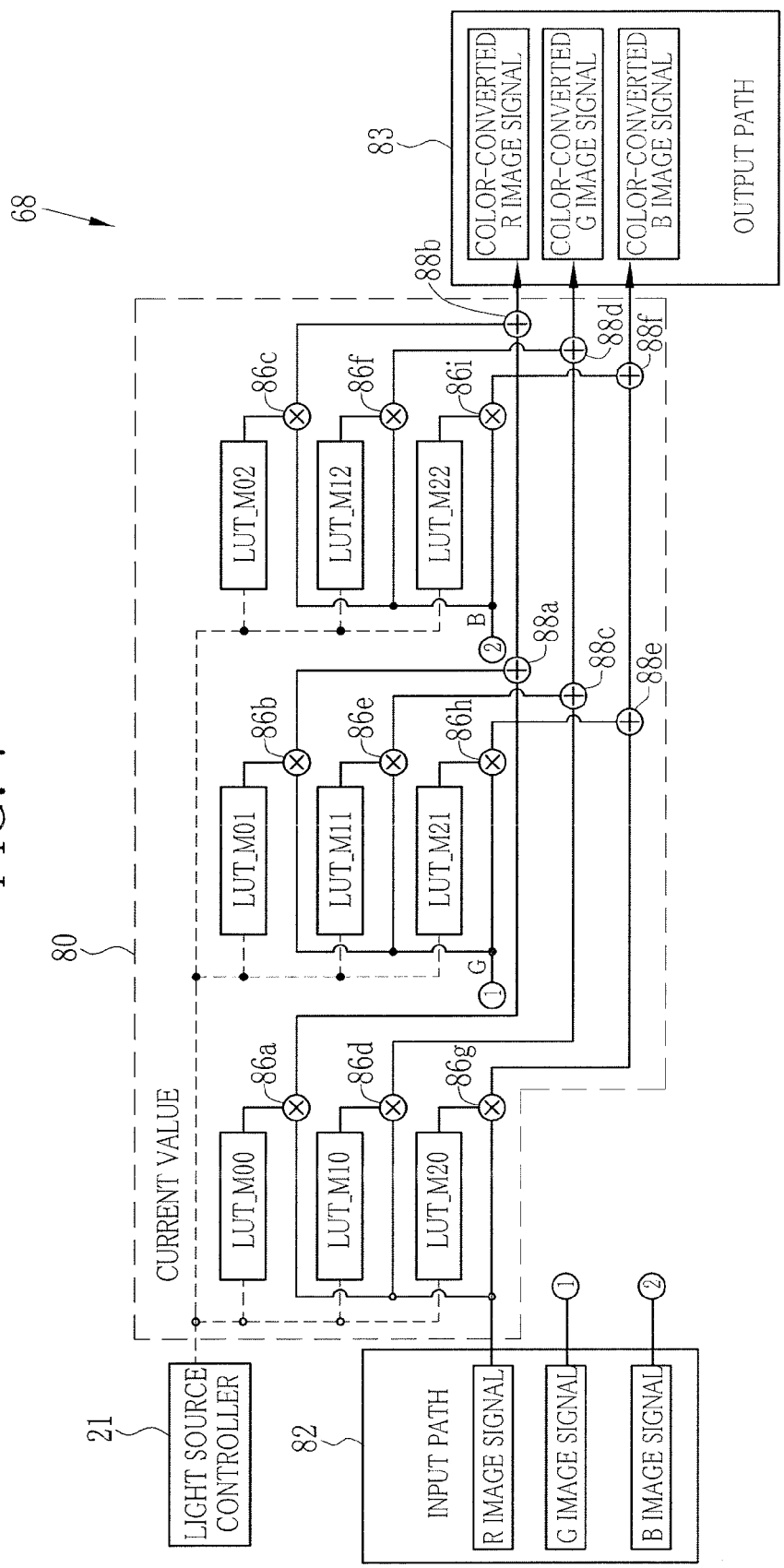
FIG. 7 is a block diagram schematically illustrating the functions of a normal color converter according to the first embodiment.

As illustrated in FIG. 7, the normal color converter 68 has a 3×3 matrix circuit 80 (array processor), an input path 82 for RGB image signals, an output path 83 for RGB image signals, nine tables of LUT_Mij (each of i and j is any number of 0, 1 and 2; corresponding to a table memory of the present invention), multipliers 86a-86i, and adders 88a-88f. Each LUT_Mij stores a first matrix coefficient Mij_c (c is 0 or an integer of 1-1023) corresponding to the 10-bit current value "c" of the R-LED 20d. The first matrix coefficient Mij_c is a parameter for correcting the wavelength shift or aging degradation of the R-LED 20d.

Each LUT_Mij is connected between the light source controller 21 and the multipliers 86a-86i in the light source apparatus 14. Upon inputting the current value "c" of the R-LED 20d from the light source controller 21, the LUT_Mij outputs the first matrix coefficient Mij_c corresponding to the inputted current value "c". Each of the multipliers 86a-86i multiplies the RGB image signals from the input path 82 by the outputted first matrix coefficient Mij_c.

The adder 88a adds the R image signal multiplied by a first matrix coefficient M00_c to the G image signal multiplied by a first matrix coefficient M01_c. The adder 88b adds the B image signal multiplied by a first matrix coefficient M02_c to the image signal outputted from the adder 88a. The image signal passed through the adder 88b is outputted as a color-converted R-image signal represented by the following expression (1) from the output path 83.

$$\text{Color-converted } R \text{ image signal} = M00\_c \times R \text{ image signal} + M01\_c \times G \text{ image signal} + M02\_c \times B \text{ image signal} \quad (1)$$

Performing operations by the adders 88c-88f allows output of a color-converted G image signal and a color-converted B image signal represented by the following expressions (2) and (3), respectively, from the output path 83.

$$\text{Color-converted } G \text{ image signal} = M10\_c \times R \text{ image signal} + M11\_c \times G \text{ image signal} + M12\_c \times B \text{ image signal} \quad (2)$$

$$\text{Color-converted } B \text{ image signal} = M20\_c \times R \text{ image signal} + M21\_c \times G \text{ image signal} + M22\_c \times B \text{ image signal} \quad (3)$$

Note that the correlation between the current value "c" of the R-LED 20d and the first matrix coefficient Mij stored in each LUT_Mij is obtained by initial measurement at the time of shipping the endoscope system 10 and determined as follows. First, a minimum current value "Cmin" is applied to the R-LED 20d to emit the red light R, and the object of interest is imaged under irradiation with the red light R to output the RGB image signals. A first matrix coefficient Mij_0 is determined based on the outputted RGB image signals and target RGB image signals. The determined first matrix coefficient Mij_0 is stored to the LUT_Mij. Then, the current value "c" to be applied to the R-LED 20d is gradually increased. At each time that the current value "c" is increased, a first matrix coefficient Mij_p (p is an integer of 1-1023) is calculated and stored to the LUT_Mij.

Figure 18:
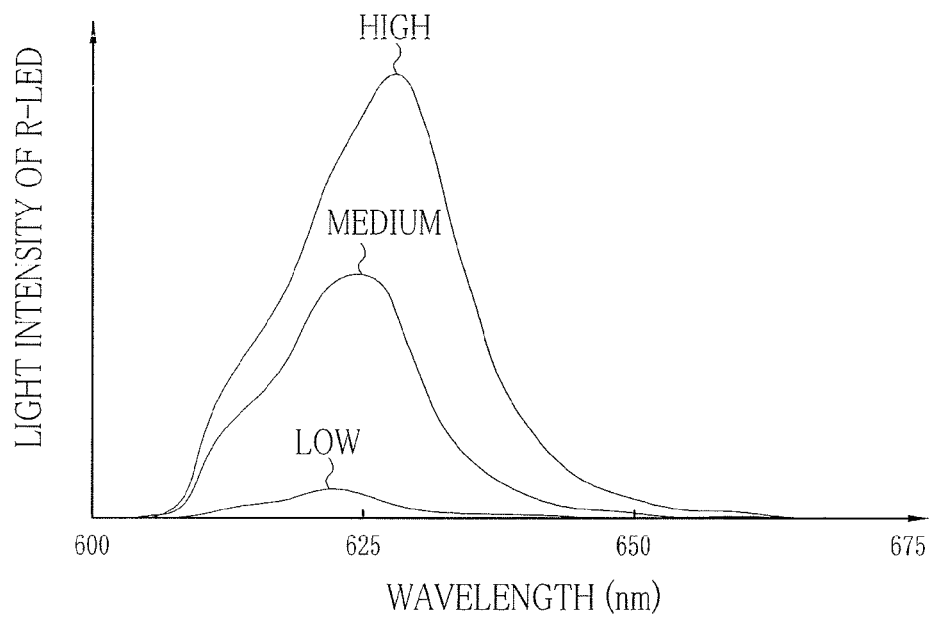
FIG. 18 is a graph illustrating spectral light intensity of an R-LED.
Figure 19:
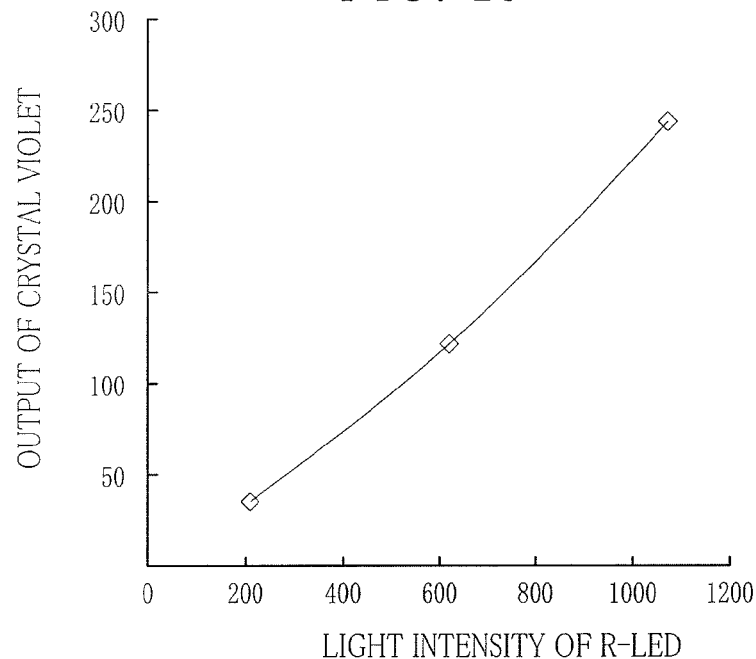
FIG. 19 is a graph illustrating the relation between the light intensity of the R-LED and an output value (a value of a reflected light amount) of crystal violet.
Figure 20:
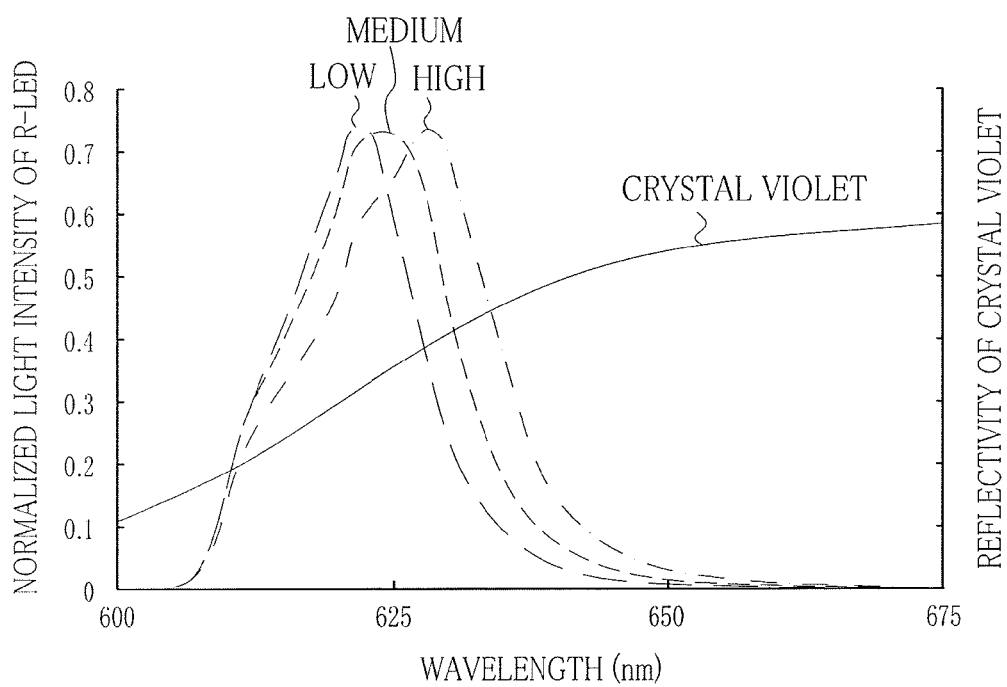
FIG. 20 is a graph illustrating a normalized intensity of the R-LED and spectral reflectivity of the crystal violet.

Note that the peak wavelength of the R-LED shifts to the long wavelength side with an increase in the light intensity, in other words, with an increase in the current value "c" (see FIGS. 18 and 20), and therefore, the first matrix coefficient Mij_c is so determined as to correct a change in a color tone associated with the wavelength shift. In imaging with dye of the crystal violet, for example, redness in the image becomes strong as the light intensity of the R-LED increases. To correct the redness, the first matrix coefficients M00_c, M01_c and M02_c are so determined as to lower the color-converted R image signal in a case where the current value "c" exceeds a predetermined value. For example, M00_c by which the R image signal is multiplied may be decreased, or M01_c and M02_c by which the G image signal and the B image signal are multiplied, respectively, may be increased.

The second image processing device 64 includes the special color converter 74, a special color enhancer 76 and a special image enhancer 78 (structural enhancer). The second image processing device produces the special light image in which a specific structure such as superficial blood vessels are enhanced. The special color converter 74 applies color conversion processing to the RGB three channels of digital image signals, and outputs color-converted RGB image signals. The special color converter 74 prevents a change in a color tone caused by the wavelength shift and aging degradation of the R-LED 20d in the same manner as the normal color converter 68, and also applies matrix operation for pseudocolor expression of the special light image.

Moreover, the special color converter 74 applies gradation conversion processing to the color-converted RGB image signals to output gradation-converted RGB image signals. The special color enhancer 76 applies various types of color enhancement processing to the gradation-converted RGB image signals. The special image enhancer 78 applies structural enhancement processing (image enhancement) to the color-enhanced RGB image signals, for example, sharpness processing, edge enhancement processing and the like. The RGB image signals, after being subjected to the structural enhancement processing by the special image enhancer 78, are inputted to the video signal generator 66.

The video signal generator 66 converts the RGB image signals inputted from the first or second image processing device 62 or 64 into video signals displayable on the monitor display panel 18. Based on the converted video signals, the monitor display panel 18 displays the normal light image in the normal imaging mode, and the special light image in the special imaging mode.

Figure 8:
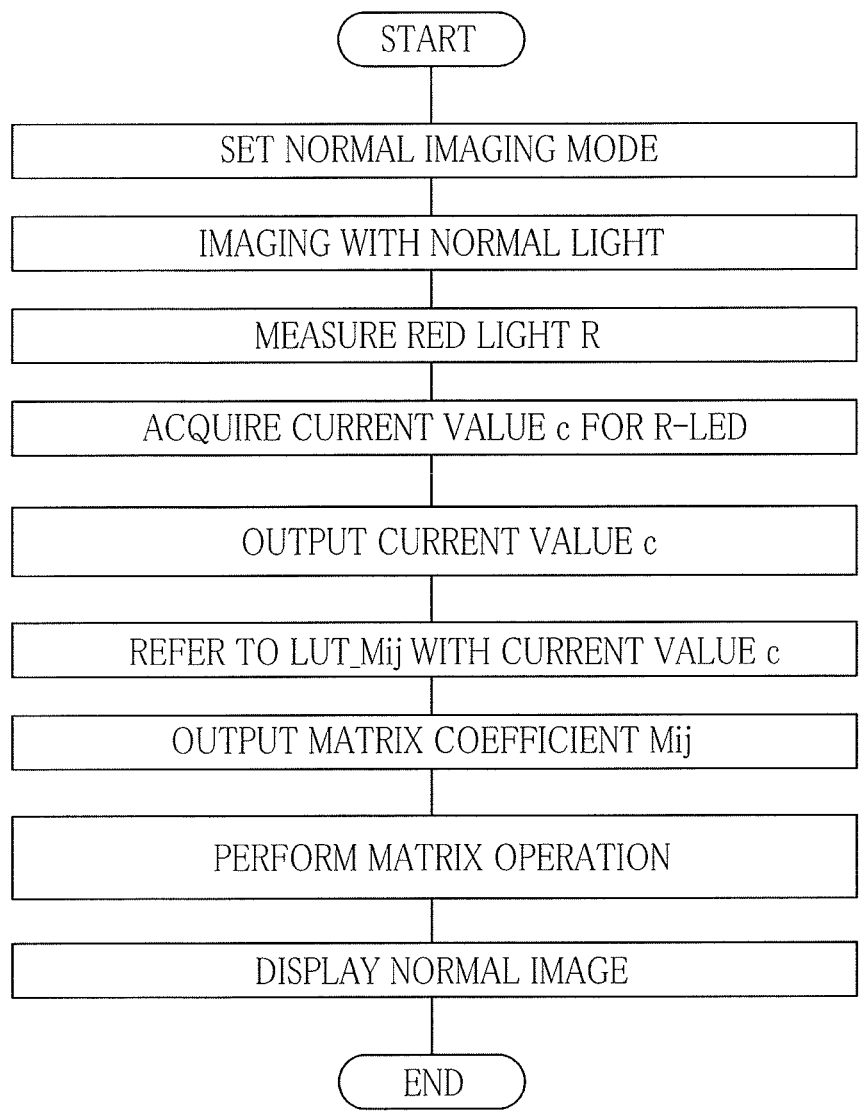
FIG. 8 is a flowchart illustrating a sequential flow of a normal imaging mode according to the first embodiment.

Next, the operation of the present invention will be described with referring to a flowchart of FIG. 8. Upon setting the normal imaging mode by operating the mode selection button 13a, all of the V-LED 20a, the B-LED 20b, the G-LED 20c and the R-LED 20d are turned on. Thus, the normal light being mixture of the narrow band violet light Vn, the narrow band blue-green light Bn, the green light G and the red light R is applied to an object of interest in a body. The image sensor 48 images the object of interest irradiated with the normal light. The image sensor 48 outputs the RGB image signals.

In the light source apparatus 14, the measurement sensor 25 measures the light amount of the red light R emitted from the R-LED 20d. The light amount signal measured by the measurement sensor 25 is outputted to the light source controller 21. The light source controller 21 compares the light amount signal with the target light amount signal outputted from the light amount acquisition device 54 of the processing apparatus 16, and determines the current value "c" to be applied to the R-LED 20d based on the comparison result such that the emitted light amount of the R-LED 20d coincides with the target light amount. The determined current value "c" is outputted to the R-LED 20d and also to the normal color converter 68 in the processing apparatus 16.

The current value "c" of the R-LED 20d outputted from the light source controller 21 is inputted to the 3×3 matrix circuit 80 of the normal color converter 68. In the 3×3 matrix circuit 80, the current value "c" is inputted to each LUT_Mij. Each LUT_Mij outputs the first matrix coefficient Mij_c corresponding to the inputted current value "c". The RGB image signals are subjected to the matrix operation based on the outputted first matrix coefficient Mij_c. Thus, the color-converted RGB image signals are obtained. The normal light image is produced from the color-converted RGB image signals, and displayed on the monitor display panel 18. In the normal light image, a change in a color tone associated with the wavelength shift and aging degradation of the R-LED 20d is prevented.

Second Embodiment

In the first embodiment, the matrix operation is performed in such a state that first matrix coefficients Mij_c (each of i and j is any one of 0, 1 and 2, and c is 0 or an integer of 1-1023) corresponding to every current value "c" of the R-LED are stored in the LUT_Mij in the 3×3 matrix circuit 80. However, this may require huge capacity of a memory. According to a second embodiment, first matrix coefficients Mij_c corresponding to every current value "c" of the R-LED are stored in a bulk storage medium other than the LUT_Mij in the 3×3 matrix circuit 80, and the first matrix coefficients Mij_c are read out of the bulk storage medium as necessary, to perform the matrix operation.

Figure 9:
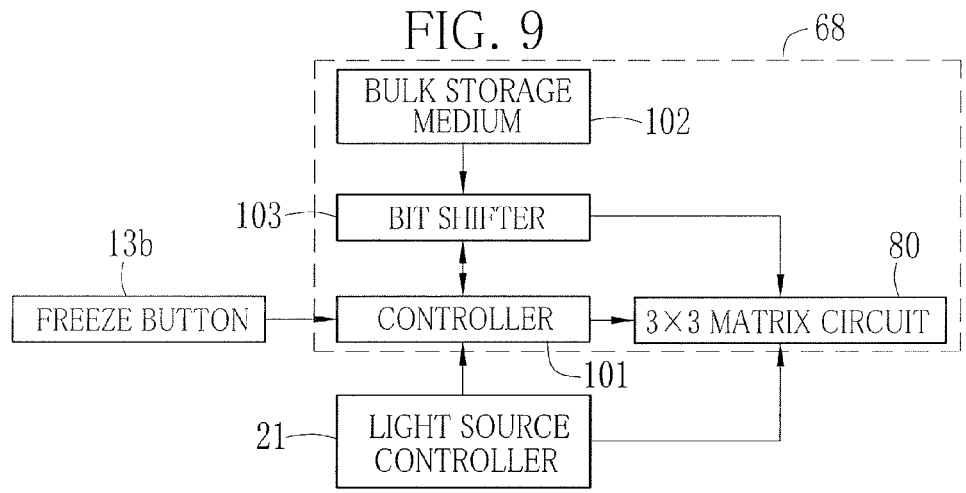
FIG. 9 is a block diagram schematically illustrating the functions of a normal color converter according to a second embodiment.
Figure 10:
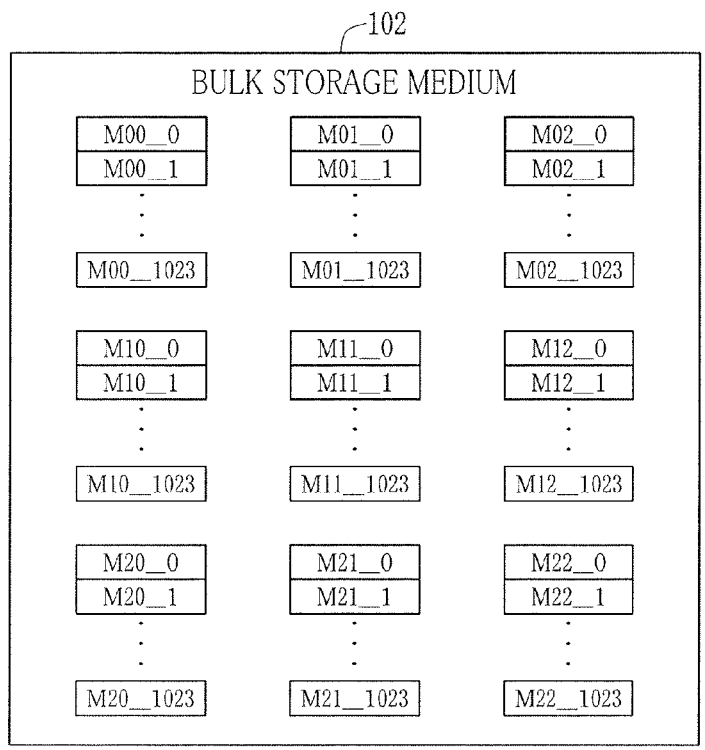
FIG. 10 is an explanatory view of a bulk storage medium stored with first matrix coefficients Mij.

As illustrated in FIG. 9, a normal color converter 68 according to the second embodiment includes a controller 101, a bulk storage medium 102 (or bulk memory) and a bit shifter 103, in addition to the 3×3 matrix circuit 80 of the first embodiment. To the controller 101 connected to the light source controller 21, the current value "c" is inputted from the light source controller 21. To the controller 101 connected to the freeze button 13b, the freeze signal is inputted from the freeze button 13b. The controller 101 is also connected to the bulk storage medium 102 through the bit shifter 103, which is connected to the 3×3 matrix circuit 80. As illustrated in FIG. 10, the bulk storage medium 102 stores the first matrix coefficients Mij_c (each of i and j is any one of 0, 1 and 2, and c is 0 or an integer of 1-1023) corresponding to the 10 bits of current values "c" of the R-LED 20d. Note that the special color converter 74 as described above is repeated in the second embodiment.

In the moving image mode in which no freeze signal is inputted to the processing apparatus 16, the controller 101 reads out only a part of the matrix coefficients Mij from the bulk storage medium 102, and operates to store the part of the first matrix coefficients Mij to the LUT_Mij in the 3×3 matrix circuit 80 (with discreteness from one another) to perform the matrix operation. Thus, it is possible to reduce the number of the first matrix coefficients Mij stored in the LUT_Mij, and therefore, reduce memory capacity. For example, as illustrated in FIG. 10, although a memory capacity of 3×3×1024 is required for storing every first matrix coefficient corresponding to all actual levels of the current value in each LUT_Mij, but a memory capacity of 3×3×8 is enough in the case of thinning out the first matrix coefficients Mij at intervals of 7 bits (128).

On the other hand, in the still image mode in which the freeze signal is inputted to the processing apparatus 16, the controller 101 reads out the first matrix coefficients Mij corresponding to the current value "c" from the bulk storage medium 102, and directly performs the matrix operation based on the read first matrix coefficients Mij. Thus, the LUT_Mij in the 3×3 matrix circuit 80 is not used in the still image mode.

Figure 11:
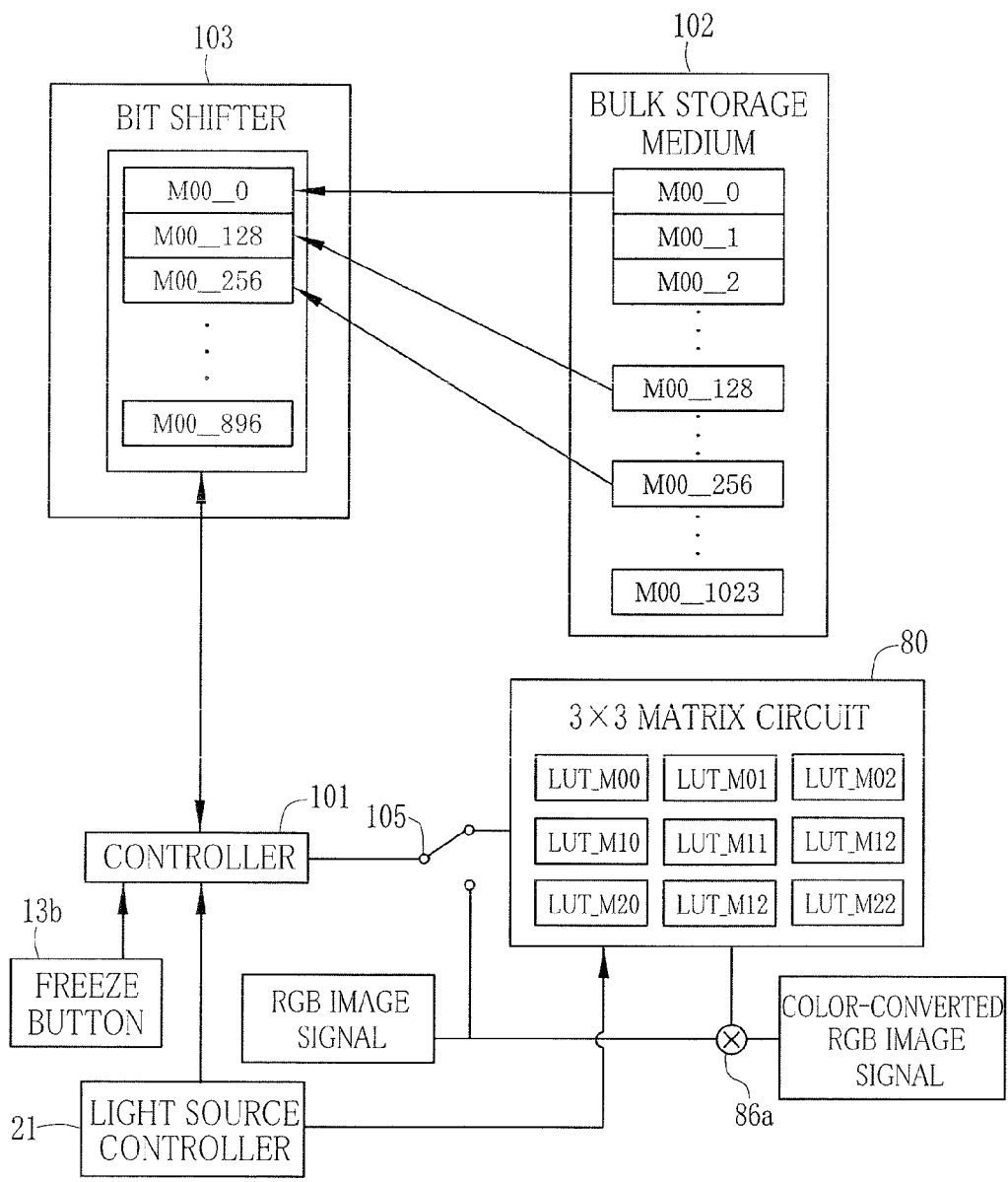
FIG. 11 is an explanatory view of the operation of the normal color converter during displaying a moving image.

The following operation is carried out for readout of first matrix coefficients M00. In the moving image mode, as illustrated in FIG. 11, the bit shifter 103 thins out the first matrix coefficients M00 and reads e.g. M00_0, M00_128, M00_256, ..., M00_896 among M00_0 to M00_1023 in the bulk storage medium 102. The thinned out first matrix coefficients M00 are stored in the LUT_M00. Then, the LUT_M00 is set in a connected state to the multiplier 86a through a coefficient selection device 105. In the moving image mode, the matrix operation is performed based on the first matrix coefficients stored in the LUT_M00. For example, upon inputting the current value "c", one of the first matrix coefficients corresponding to one of plural current values within a prescribed range including the inputted current value "c" is chosen from the first matrix coefficients stored in the LUT_M00. An example of one current value is a particular current value the nearest to the inputted current value "c" (corresponding to a particular drive value in the invention). The matrix operation is performed based on the chosen first matrix coefficient.

Figure 12:
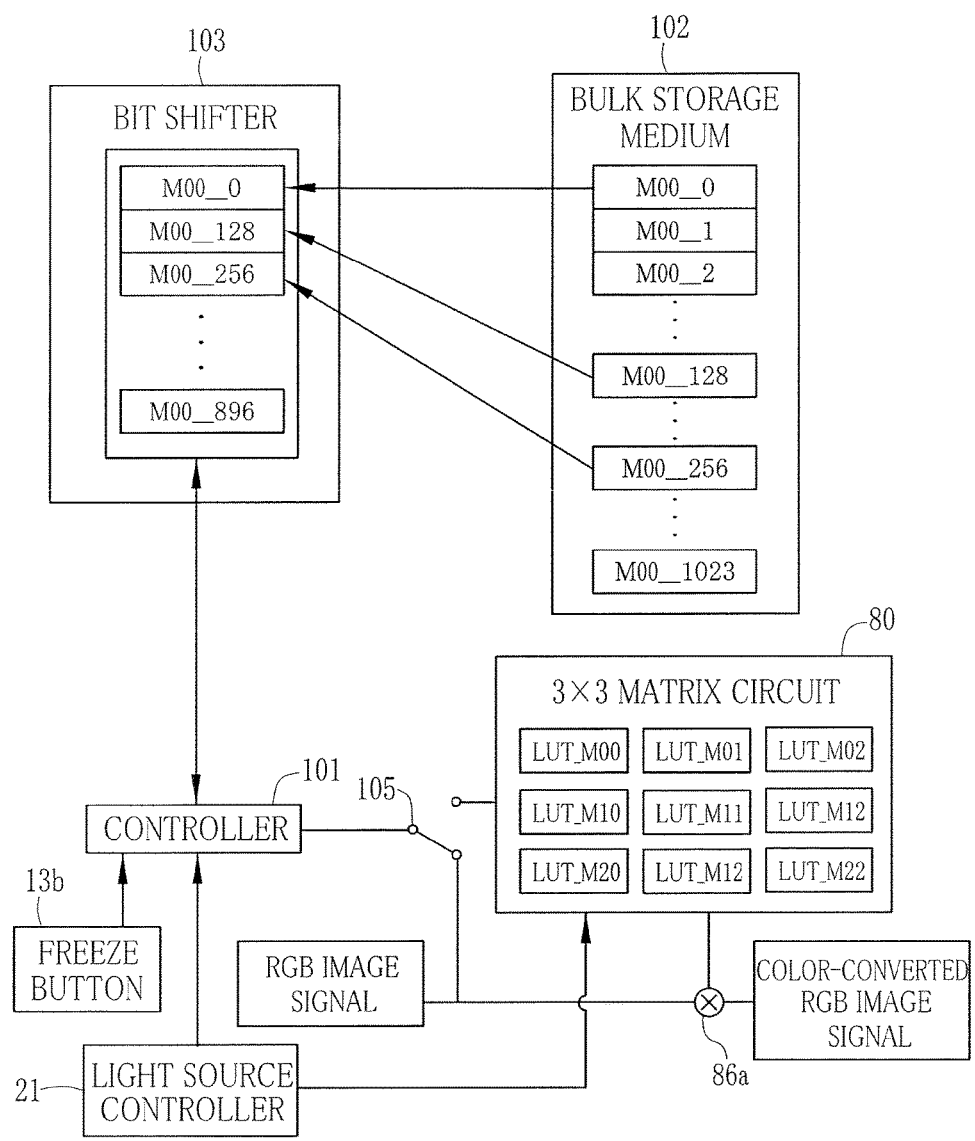
FIG. 12 is an explanatory view of the operation of the normal color converter during capturing a still image.

On the other hand, in the still image mode, as illustrated in FIG. 12, the coefficient selection device 105 disconnects between the LUT_M00 and the multiplier 86a, and connects the controller 101 to the multiplier 86a. Then, the first matrix coefficient M00 corresponding to the current value "c" is read out of the bulk storage medium 102. The multiplier 86a multiplies the R image signal directly by the read first matrix coefficient M00 without use of the LUT_M00. Likewise, the first matrix coefficients M01-M22 are read out just as with the first matrix coefficients M00.

Note that, according to the second embodiment, in the still image mode, the first matrix coefficient corresponding to the current value "c" is read out of the bulk storage medium 102 and the matrix operation is performed with the use of this first matrix coefficient. Instead of this, processing of interpolation may be performed based on the first matrix coefficients Mij stored during the moving image mode in the LUT_Mij of the matrix circuit 80, so that the matrix operation may be performed with the use of a first matrix coefficient obtained by the interpolation processing. Taking a case where the LUT_Mij stores the first matrix coefficients Mij that are thinned out at intervals of 7 bits (128) of current values as an example, the interpolation processing to be carried out at a current value "c" of 128-256 is expressed in the following equation (4):

$$Mij\_c = ((c-128) \times Mij\_256 + (256-c) \times Mij\_128)/128 \quad (4)$$

Third Embodiment

According to the above first and second embodiments, the matrix operation corrects a change in a color tone associated with the wavelength shift and aging degradation of the R-LED. In addition to this, matrix operation may correct a change in a color tone caused by individual difference between endoscopes, in other words, variations in spectral sensitivity of the image sensors 48. In a third embodiment, calibration is performed before starting an endoscopic diagnosis to calculate a second matrix coefficient CMij (each of i and j is any one of 0, 1 and 2) for use in absorption of the individual difference between the endoscopes, that is to say, correction of variations in the spectral sensitivity of the image sensors 48. Then, as represented by the following expression (5), the matrix operation is performed in a similar manner to the first and second embodiments with the use of a corrected matrix coefficient Mij_c', which is obtained by a multiplication of the first and second matrix coefficients Mij_c and CMij.

$$Mij\_c' = CMij \times Mij\_c \quad (5)$$

Figure 13:
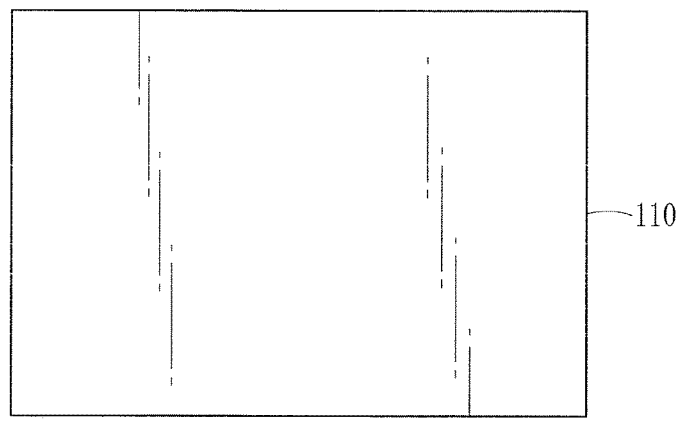
FIG. 13 is a plan view of a white plate.

A method of calculating the second matrix coefficients (nine coefficients of CM00-CM22) by the calibration is as follows. First, four components of monochromatic light i.e. the narrow band violet light Vn, the narrow band blue-green light Bn, the green light G and the red light R are sequentially applied to a white plate 110 as illustrated in FIG. 13. Upon applying each component of light, the image sensor 48 outputs three color image signals, that is, an R image signal, a G image signal and a B image signal. Accordingly, by the application of the monochromatic light components, twelve image signals (application of four components of light×three color image signals) are obtained in total.

Then, six combinations of two-color mixture light each of which is mixture of light of two colors out of the narrow band violet light Vn, the narrow band blue-green light Bn, the green light G and the red light R are sequentially applied. Upon applying each combination of two-color mixture light, the image sensor 48 outputs three color image signals, that is, an R image signal, a G image signal and a B image signal. Then, by the application of the two-color mixture light, eighteen image signals (application of six combinations of light×three color image signals) are obtained in total. Furthermore, four combinations of three-color mixture light each of which is mixture of light of three colors out of the narrow band violet light Vn, the narrow band blue-green light Bn, the green light G and the red light R are sequentially applied. Upon applying each combination of three-color mixture light, the image sensor 48 outputs three color image signals, that is, an R image signal, a G image signal and a B image signal. Accordingly, by the application of the three-color mixture light, 12 image signals (application of four combinations of light×three color image signals) are obtained in total.

In closing, the normal light is applied by simultaneously turning on all of the LEDs. Also, while every LED is turned off, zero light (no light or Bk light) is applied. Upon applying each condition of light, the image sensor 48 outputs three color image signals, that is, an R image signal, a G image signal and a B image signal. Accordingly, by the application of the normal light and the zero light, six image signals (application of two conditions of light×three color image signals) are obtained in total.

As described above, the application of the monochromatic light, the two-color mixture light, the three-color mixture light, the normal light and the zero light results in obtaining 48 image signals in total. The second matrix coefficients (CM00-CM22) are calculated based on the obtained 48 image signals and 48 target image signals. Note that the second matrix coefficients are calculated using 48 colors of light, but may be calculated using fewer colors of light than 48.

Note that, in the case of an endoscope system having three color LEDs e.g. an R-LED, a G-LED and a B-LED (unlike the endoscope system having the four color LEDs such as the V-LED 20a, the B-LED 20b, the G-LED 20c and the R-LED 20d as described in this embodiment), the second matrix coefficients are calculated as follows. First, light is applied to the white plate 110 (see FIG. 13) in the following order, "R light (turn on the R-LED)", "G light (turn on the G-LED)", "B light (turn on the B-LED)", "C light (simultaneously turn on the B-LED and G-LED)", "M light (simultaneously turn on the B-LED and R-LED)", "Y light (simultaneously turn on the G-LED and R-LED)", "W light (simultaneously turn on the B-LED, G-LED and R-LED)", and "zero light (turn off all of the B-LED, G-LED and R-LED)". Upon applying each light, the image sensor 48 outputs three color image signals, that is, an R image signal, a G image signal, and a B image signal. Thus, twenty-four image signals (application of eight combinations of light× three color image signals) are obtained in total. The second matrix coefficients (CM00-CM22) are calculated based on the obtained twenty-four image signals and twenty-four target image signals. Note that the second matrix coefficients are calculated using eight colors of light, but may be calculated using fewer colors of light than eight.

According to the third embodiment, the second matrix coefficients are calculated by the calibration. However, initial processing corresponding to the calibration can be performed during manufacturing the endoscope or the like to calculate the second matrix coefficients, and the calculated second matrix coefficients and product ID data of the endoscope may be stored to a memory in a related manner. In the actual use of the endoscope, in case the endoscope system is connected to the processing apparatus, an ID reader of the processing apparatus reads the product ID data, and the matrix operation is performed with the use of the second matrix coefficients corresponding to the read product ID data.

Note that this memory is provided in the normal color converter 68 in a manner similar to the bulk storage medium 102. However, the memory can be arranged in a manner readable from the processing apparatus 16.

Figure 14:
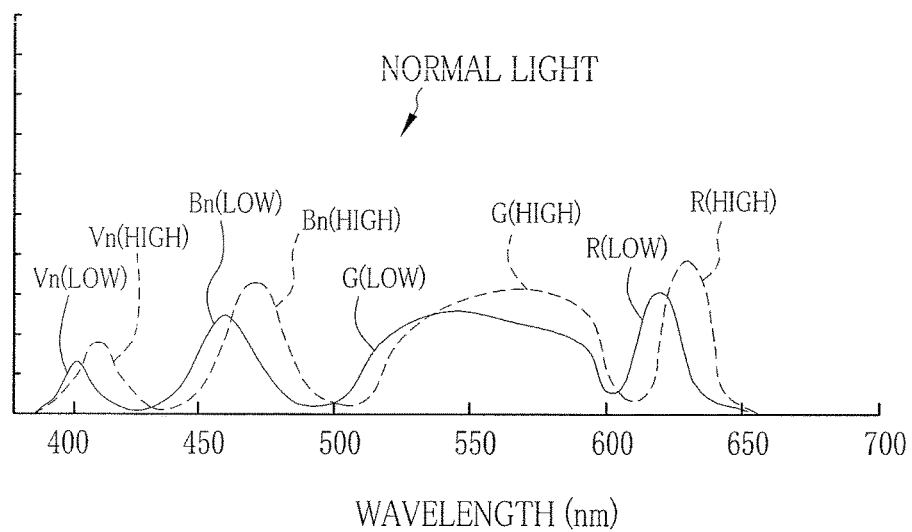
FIG. 14 is an explanatory view illustrating wavelength variation in narrow band violet light, narrow band blue-green light, green light and red light associated with an increase in light intensity.

Note that, according to the above first to third embodiments, only the emitted light amount of the R-LED 20d is measured, and the matrix operation is performed in the processing apparatus based on the measurement result. However, a wavelength shift occurs to the other colors of the V-LED 20a, the B-LED 20b and the G-LED 20c, in such a manner that the center wavelengths of the narrow band violet light Vn, the narrow band blue-green light Bn and the green light G shift to the long wavelength side with an increase in the light intensity, as illustrated in FIG. 14. In FIG. 14, the light intensity is higher at "Vn(high)" than at "Vn(low)". The light intensity is higher at "Bn(high)" than at "Bn(low)". The light intensity is higher at "G(high)" than at "G(low)". The light intensity is higher at "R(high)" than at "R(low)".

Figures 15, 16:
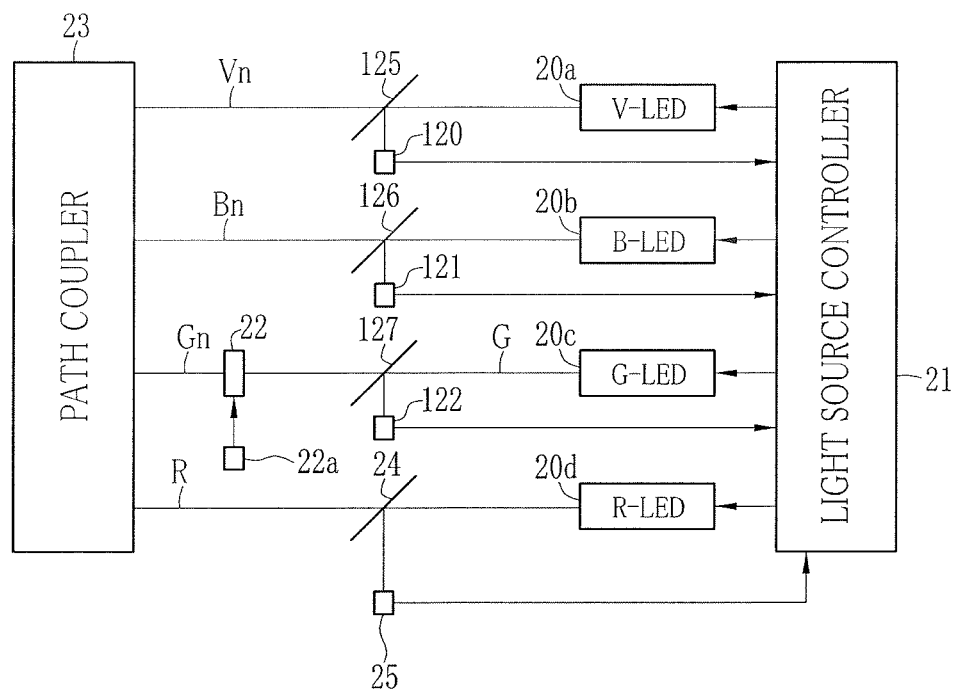
FIG. 15 is a block diagram schematically illustrating a path coupler and light amount measurement sensors for measuring the amount of the narrow band violet light, the narrow band blue-green light, the green light and the red light.
FIG. 16 is an explanatory view of a three dimensional look-up table (3D LUT)

Thus, the emitted light amount of each of the V-LED 20a, the B-LED 20b and the G-LED 20c may be measured, and the matrix operation may be performed based on the measurement result. As illustrated in FIG. 15, measurement sensors 120-122 measure the emitted light amounts of the V-LED 20a, the B-LED 20b and the G-LED 20c, respectively, as with the measurement sensor 25. The measurement sensors 120-122 measure the light amount of reflected components of the narrow band violet light Vn, the narrow band blue-green light Bn and the green light G from glass plates 125-127 (half mirrors), respectively. Note that, just as with the glass plate 24, the glass plates 125-127 pass most of the narrow band violet light Vn, the narrow band blue-green light Bn and the green light G to the path coupler 23, and reflect a part thereof to the measurement sensors 120-122, respectively.

The light source controller 21 determines a current value to be applied to each of the LEDs 20a-20d based on the light amount signals outputted from each of the measurement sensors 25 and 120-122 and the target light amount signals of the LEDs 20a-20d. Note that "cv" represents a current value for the V-LED 20a. "cb" represents a current value for the B-LED 20b. "cg" represents a current value for the G-LED 20c, and "cr" represents a current value for the R-LED 20d. The determined current value is outputted to each of the LEDs 20a-20d and the normal and special color converters 68 and 74.

The normal and special color converters 68 and 74 perform the matrix operation in order to correct color variations caused by the wavelength shift and the like of each of the LEDs 20a-20d. To this end, the normal and special color converters 68 and 74 store not only the first matrix coefficients Mij_cr for correcting the wavelength shift and the aging degradation of the R-LED 20d, but also first matrix coefficients Mij_cv, Mij_cb and Mij_cg for correcting the wavelength shift and the aging degradation of the V-LED 20a, the B-LED 20b and the G-LED 20c in a manner related to the current values "cr", "cv", "cb" and "cg", respectively. In actually performing the matrix operation, the RGB image signals are multiplied by a product of the four first matrix coefficients corresponding to the current values "cr", "cv", "cb" and "cg" determined by the light source controller 21, that is, Mij_cv×Mij_cb×Mij_cg×Mij_cr. Therefore, it is possible to obtain color-converted RGB image signals in which the color variations caused by the wavelength shift and the like are corrected.

Note that the change in a color tone associated with the wavelength shift and the aging degradation of the R-LED 20*d* is corrected by using the 3×3 matrix circuit 80 in the above first to third embodiments, but may be corrected by using a three-dimensional look-up table (3D LUT corresponding to a table memory of the present invention). As illustrated in FIG. 16, the RGB image signals and the color-converted RGB image signals are stored in a related manner in a 3D look-up table 130 (LUT). In response to an input of the RGB image signals, the color-converted RGB image signals are outputted. There are a plurality of 3D look-up tables 130 in association with plural levels of the current value of the R-LED 20*d*.

Accordingly, in actually performing the matrix operation, the 3D LUT corresponding to the current value to be applied to the R-LED 20*d* is chosen from the plural 3D look-up tables 130. By using the chosen 3D LUT, the RGB image signals are converted into the color-converted RGB image signals. There is a conceivable method for producing the 3D LUTs, in which a large number of correlations between the RGB image signals obtained under light emitted at a predetermined current value and the color-converted RGB image signals can be stored in association with the current value. Based on the stored correlation between the current values, the RGB image signals and the color-converted RGB image signals, the 3D LUTs can be produced.

Figure 17:
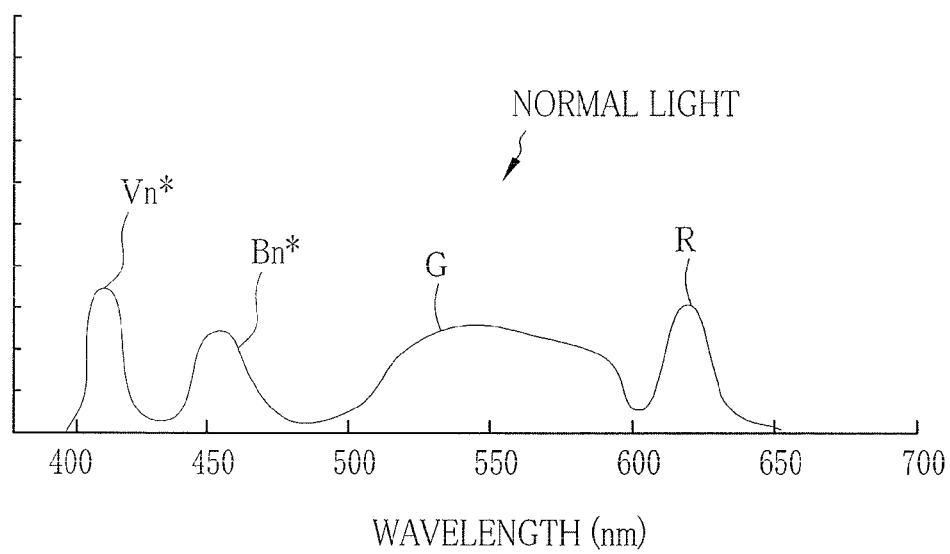
FIG. 17 is a graph of an emission spectrum of normal light different from FIG. 3.

Note that the four colors of light having emission spectra as illustrated in FIG. 3 are used in the above embodiment, but light having different spectra may be used instead. For example, as illustrated in FIG. 17, while green light G and red light R have the same spectra as FIG. 3, narrow band violet light Vn* has a center wavelength of 410-420 nm and a wavelength range on a little longer wavelength side than the wavelength range of the narrow band violet light Vn of FIG. 3. Narrow band blue-green light Bn* has a center wavelength of 445-460 nm and a wavelength range on a little shorter wavelength side than the wavelength range of the narrow band blue-green light Bn of FIG. 3.

In the above embodiments, the R-LED of FIG. 2 is turned on to measure the red light amount for the purpose of the color conversion. However, one of the LEDs of any one of the colors can be turned on to measure a light amount of light of its color. Note that the effect of the invention can be achieved typically in the method of measuring the light amount of at least the R-LED in the mode of the normal light imaging, in view of the purpose of suppressing unwanted strength of the redness of body tissue due to a wavelength shift of the R-LED.

The endoscope system in the above embodiments is changeable between the normal light imaging and the special light imaging, but can be constructed only for the normal light imaging or for the special light imaging.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
    a semiconductor light source apparatus for emitting light to illuminate an object in a body cavity;
    a measurement sensor for measuring a light amount of said light;
    a light source controller for setting a drive value of said light source apparatus according to said light amount of said light from said measurement sensor;
    an image sensor for imaging said object illuminated with said light to obtain a first color image signal of a color image;
    a color converter for performing color conversion of said first color image signal into a second color image signal, and adjusting a setting of said color conversion according to said drive value of said light source apparatus that was set,
    wherein said color conversion includes a matrix operation of converting said first color image signal into said second color image signal according to a first matrix coefficient, and said first matrix coefficient is changeable according to said set drive value, and
    wherein the first matrix coefficient corresponds to each of bit converted values of the drive value.

2. An endoscope system as defined in claim 1, further comprising a table memory for storing said drive value of said light source apparatus and said first matrix coefficient associated with said drive value, said table memory being accessed for said matrix operation by said color converter.

3. An endoscope system as defined in claim 1, further comprising:
    a table memory for storing a particular drive value usable in said light source apparatus and predetermined with discreteness, and said first matrix coefficient associated with said particular drive value;
    a storage medium for storing an actual drive value for said light source apparatus in smaller steps than said particular drive value, and said first matrix coefficient associated with said actual drive value;
    wherein in case a moving image mode is set, said color converter refers to said particular drive value in said table memory according to said set drive value to read out said first matrix coefficient, and in case a still image mode is set, said color converter refers to said set drive value in said storage memory to read out said first matrix coefficient.

4. An endoscope system as defined in claim 1, further comprising a table memory for storing a particular drive value usable in said light source apparatus and predetermined with discreteness, and said first matrix coefficient associated with said particular drive value;
    wherein in case a moving image mode is set, said color converter refers to said particular drive value in said table memory according to said set drive value to read out said first matrix coefficient;
    in case a still image mode is set, said color converter interpolates said first matrix coefficient from said table memory by use of said set drive value, to acquire an interpolated value of said first matrix coefficient.

5. An endoscope system as defined in claim 1, wherein in said matrix operation, said first color image signal is further processed in a matrix control according to a second matrix coefficient different from said first matrix coefficient, and said second matrix coefficient is variable according to spectral sensitivity of said image sensor.

6. An endoscope system as defined in claim 5, wherein said light source apparatus includes a plurality of semiconductor light sources of colors for applying said light to said object one after another in relation to said colors;

said color converter obtains said second matrix coefficient according to said first color image signal generated upon imaging of said image sensor with said light of said colors.

7. An endoscope system as defined in claim 5, further comprising a memory for storing product ID data of said endoscope having said image sensor and said second matrix coefficient associated with said product ID data, said memory being accessed for said matrix operation by said color converter.

8. An endoscope system as defined in claim 1, further comprising a table memory for storing said first color image signal and said second color image signal associated with said first color image signal, said table memory being accessed for said color conversion by said color converter;
wherein said table memory is associated with each one of levels of the drive value of said light source apparatus.

9. An endoscope system as defined in claim 1, wherein said light source apparatus includes an LED.

10. An endoscope system as defined in claim 1, wherein said light source apparatus includes at least blue, green and red light sources, said measurement sensor measures said light amount of said red light source, and said light source controller sets said set drive value of said red light source.

11. An endoscope system as defined in claim 1, wherein said light source apparatus includes light sources of first to Nth colors where N is an integer, and said measurement sensor is constituted by first to Nth measurement sensors for respectively measuring said light amount of said light sources of said first to Nth colors.

12. An operating method of operating an endoscope system, comprising steps of:
emitting light from a semiconductor light source apparatus to illuminate an object in a body cavity;
measuring a light amount of said light;
setting a drive value of said light source apparatus according to said light amount of said light;
imaging said object illuminated with said light to obtain a first color image signal of a color image;
performing color conversion of said first color image signal into a second color image signal; and
adjusting a setting of said color conversion according to said drive value of said light source apparatus that was set,
wherein said color conversion includes a matrix operation of converting said first color image signal into said second color image signal according to a first matrix coefficient, and said first matrix coefficient is changeable according to said set drive value, and
wherein the first matrix coefficient corresponds to each of bit converted values of the drive value.

13. The endoscope system as defined in claim 1, wherein the drive value includes current values applied to semiconductor light sources of the semiconductor light source apparatus.

14. An endoscope system comprising:
a light source apparatus including at least one semiconductor light source for emitting light to illuminate an object in a body cavity, a measurement sensor for measuring a light amount of the light, and a light source controller;
an image sensor for imaging the object illuminated with the light to obtain a first color image signal of a color image;
a light amount acquisition device for calculating a target light amount based on the first color image signal; and
a color converter for performing color conversion of the first color image signal into a second color image signal,
wherein the light source controller sets a drive value applied to the at least one semiconductor light source based on a comparison between the light amount of the light measured by the measurement sensor and the target light amount calculated by the light amount acquisition device, and
wherein the color converter changes a setting of said color conversion according to the drive value of the at least one semiconductor light source,
wherein said color conversion includes a matrix operation of converting said first color image signal into said second color image signal according to a first matrix coefficient, and said first matrix coefficient is changeable according to said set drive value, and
wherein the first matrix coefficient corresponds to each of hit converted values of the drive value.

* * * * *